United States Patent
Shearer et al.

(10) Patent No.: US 10,209,181 B2
(45) Date of Patent: Feb. 19, 2019

(54) PLANT MATTER SENSOR TO DETERMINE HEALTH AND/OR NUTRITIONAL CONTENT BASED ON REFLECTED SIGNALS AT VERTICALLY DISPLACED POINTS ON THE PLANT MATTER

(71) Applicant: C-Dax Limited, Hornby Christchurch (NZ)

(72) Inventors: Greig Edgeworth Shearer, Palmerston North (NZ); Jeremy Philip Henry Rowe, Ashhurst (NZ); Robert Ian Murray, Palmerston North (NZ)

(73) Assignee: C-DAX Limited, Hornby, Christchurch (NZ)

( * ) Notice: Subject to any disclaimer, the term of this patent is extended or adjusted under 35 U.S.C. 154(b) by 0 days.

(21) Appl. No.: 15/576,069

(22) PCT Filed: May 20, 2016

(86) PCT No.: PCT/NZ2016/050080
§ 371 (c)(1),
(2) Date: Nov. 21, 2017

(87) PCT Pub. No.: WO2016/186523
PCT Pub. Date: Nov. 24, 2016

(65) Prior Publication Data
US 2018/0143130 A1    May 24, 2018

(30) Foreign Application Priority Data
May 21, 2015   (NZ) ........................................ 708336

(51) Int. Cl.
G01N 21/359    (2014.01)
A01B 79/00     (2006.01)
(Continued)

(52) U.S. Cl.
CPC ......... G01N 21/359 (2013.01); A01B 79/005 (2013.01); A01C 21/007 (2013.01);
(Continued)

(58) Field of Classification Search
CPC ...... A01B 79/005; A01C 21/007; A01G 7/00; G01N 2021/8466; G01N 21/3151; G01N 21/359; G01N 33/0098
(Continued)

(56) References Cited

U.S. PATENT DOCUMENTS

| 5,389,781 A | 2/1995 | Beck et al. |
| 5,884,224 A | 3/1999 | McNabb et al. |

(Continued)

FOREIGN PATENT DOCUMENTS

| DE | 19913971 | 9/2000 |
| DE | 10002880 | 6/2001 |

(Continued)

OTHER PUBLICATIONS

International Search Report for International Application No. PCT/NZ2016/050080 dated Oct. 14, 2016 (3 pages).

*Primary Examiner* — Que T Le
(74) *Attorney, Agent, or Firm* — Merchant & Gould P.C.

(57) ABSTRACT

A plant matter sensor comprising: one or more emitters configured to emit two or more vertically spaced signals toward a plant; and one or more receivers configured to receive two or more reflected signals from the plant.

17 Claims, 17 Drawing Sheets

(51) Int. Cl.
  *A01C 21/00* (2006.01)
  *G01N 21/31* (2006.01)
  *A01G 7/00* (2006.01)
  *G01N 33/00* (2006.01)
  *G01N 21/84* (2006.01)

(52) U.S. Cl.
  CPC ............ *A01G 7/00* (2013.01); *G01N 21/3151* (2013.01); *G01N 33/0098* (2013.01); *G01N 2021/8466* (2013.01)

(58) Field of Classification Search
  USPC ............................................... 250/221, 559.4
  See application file for complete search history.

(56) References Cited

U.S. PATENT DOCUMENTS

| | | | |
|---|---|---|---|
| 6,393,927 | B1 | 5/2002 | Biggs et al. |
| 6,596,996 | B1 | 7/2003 | Stone et al. |
| 7,362,439 | B2 | 4/2008 | Franzen et al. |
| 7,412,330 | B2 | 8/2008 | Spicer et al. |
| 7,911,616 | B2 | 3/2011 | Franzen et al. |
| 7,929,141 | B2 | 4/2011 | Franzen et al. |
| 8,482,736 | B2 | 7/2013 | Franzen et al. |
| 9,733,179 | B1 * | 8/2017 | Bugbee .............. G01N 33/0098 |
| 2006/0208171 | A1 | 9/2006 | Holland |
| 2006/0290933 | A1 | 12/2006 | Holm |
| 2010/0053628 | A1 | 3/2010 | Kumagai et al. |
| 2010/0283603 | A1 | 11/2010 | Yule et al. |
| 2013/0231968 | A1 | 9/2013 | Willness |

FOREIGN PATENT DOCUMENTS

| | | |
|---|---|---|
| EP | 1394530 | 3/2004 |
| JP | 03628425 | 3/2005 |
| WO | 2001006232 | 1/2001 |
| WO | 2001046678 | 6/2001 |
| WO | 2012013388 | 2/2012 |

* cited by examiner

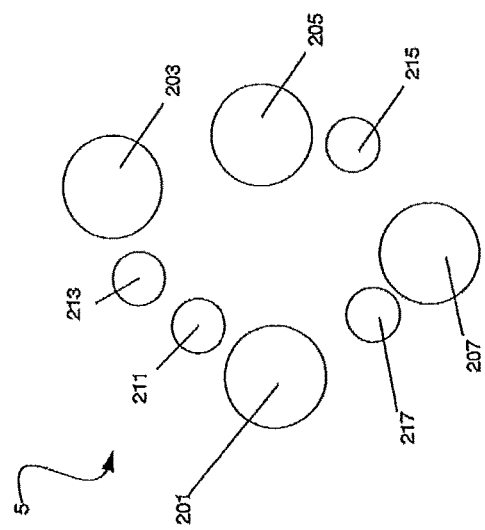
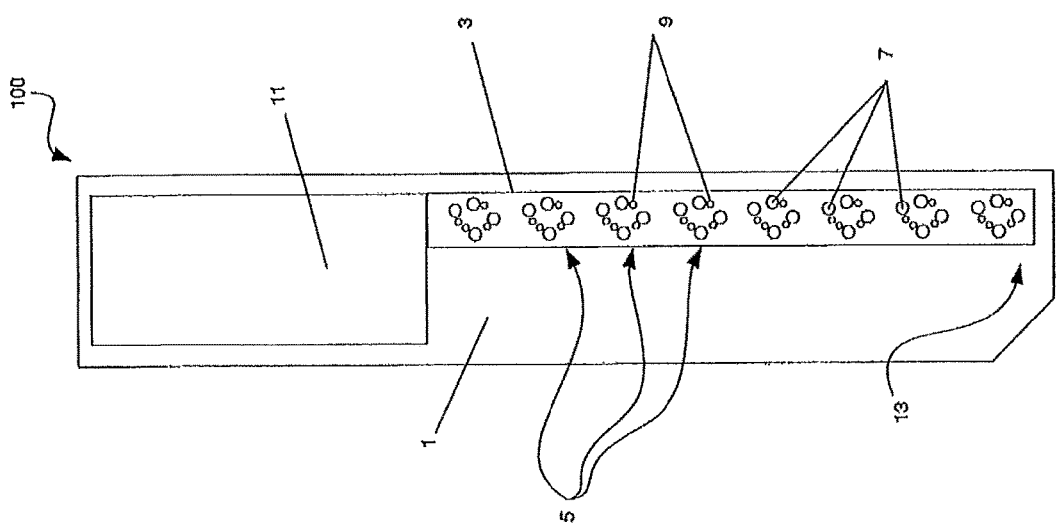

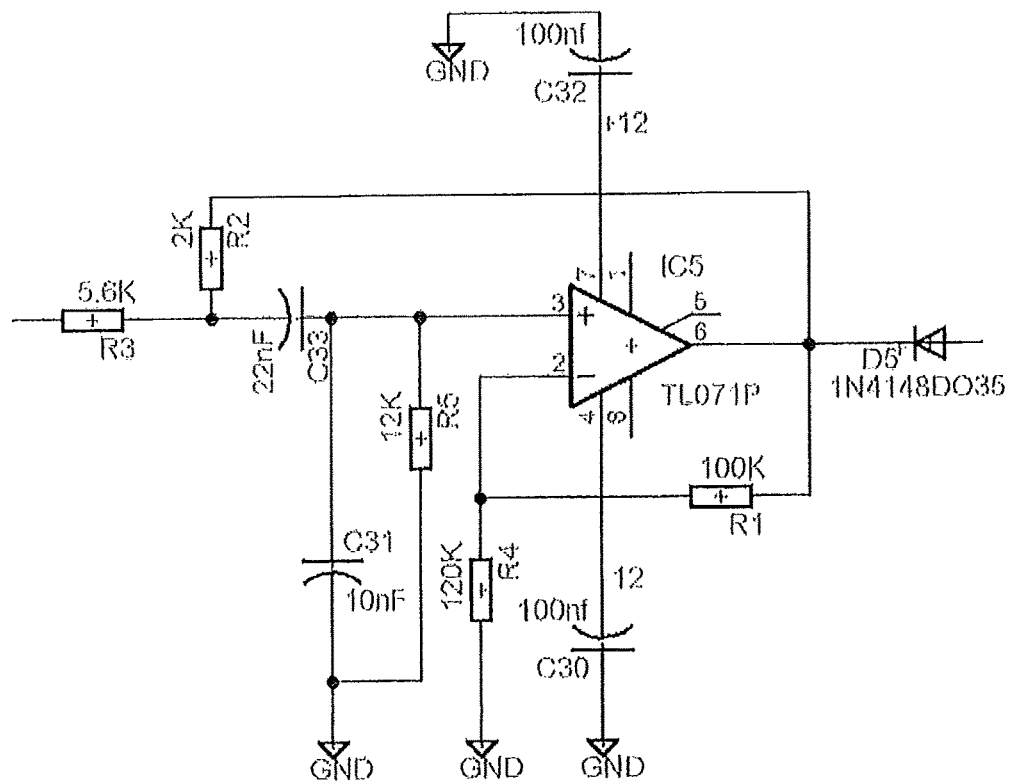
Figure 8A
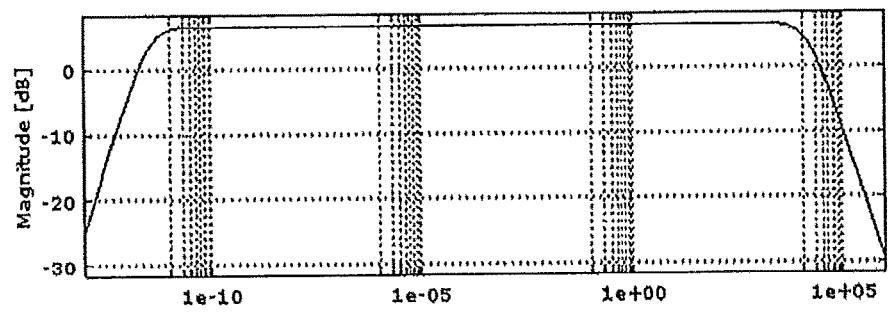
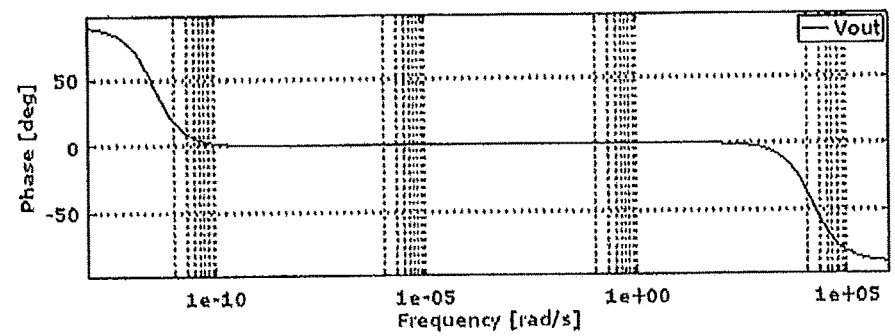
Figure 8B

PLANT MATTER SENSOR TO DETERMINE HEALTH AND/OR NUTRITIONAL CONTENT BASED ON REFLECTED SIGNALS AT VERTICALLY DISPLACED POINTS ON THE PLANT MATTER

This application is a National Stage Application of PCT/NZ2016/050080, filed 20 May 2016, which claims benefit of Serial No. 708336, filed 21 May 2015 in New Zealand and which applications are incorporated herein by reference. To the extent appropriate, a claim of priority is made to each of the above disclosed applications.

FIELD

This invention generally relates to plant matter sensors. More particularly but not exclusively, the invention relates to plant matter sensors for measuring the quantity and/or quality of plant matter using reflected signals.

BACKGROUND

It is generally recognised by commentators and researchers that the next significant frontier in agriculture is the formulation and application of precision agricultural techniques. Precision agriculture means the collection of site-specific information, application of that site-specific information in site-specific analysis, and the subsequent making of decisions in truly site-specific manner.

Fundamental to the philosophy of precision agriculture is the concept of matching site-specific inputs to site-specific needs; if a part of a field needs more fertilizer, give that part more fertilizer; if a section of a crop needs harvesting early, harvest it early. These are simple, common-sense ideas. However, like many good ideas, there is a significant gap between theory and implementation. The use of management zones is currently the most practical way to implement the theory of precision agriculture. However, this is not truly precision agriculture, as the size of the zones and the process of data collection necessarily involves a relatively significant degree of averaging which in turn impacts on how site-specific decision making can be.

One critical area ripe for application of precision agriculture techniques is in feed budgeting systems, allowing farmers to make better decisions regarding feed, production and use.

Some systems have attempted to measure pasture quality by aerial images, or from a top view of plant-matter reflectance. However, such systems only provide information about the uppermost portions of plant matter. The systems fail to provide a detailed, comprehensive measurement of the plant matter quality along the length of the plant matter, including the stem regions. Often plant matter (such as grass), may appear healthy from the top but contain dead material near its base.

Current qualitative systems (laboratory wet chemistry) do not provide the metrics in a sufficient spatial resolution and format which allows farmers to make important land and feed decisions.

Reference to any document in this specification does not constitute an admission that such document is prior art, that it is validly combinable with other documents or that it forms part of the common general knowledge.

SUMMARY

The invention may provide an improved plant matter sensor, or at least provide the public with a useful choice.

In a first aspect the invention provides a plant matter sensor including: one or more emitters configured to emit two or more vertically spaced signals toward a plant; and one or more receivers configured to receive two or more reflected signals from the plant.

In another aspect the invention provides a system for determining the quality of plant matter, including: a plant matter sensor configured measure the reflectance of plant matter along vertically displaced points on the plant matter, a vehicle configured to move the plant matter sensor through an area of plant matter, and a controller or processor configured to analyse the measured reflectance of the plant matter and determine plant matter health and/or nutritional content of the plant matter.

In a further aspect there is provided a plant matter sensor comprising: one or more emitters configured to emit two or more signals toward a plant; one or more receivers configured to receive two or more reflected signals from the plant; and a processor configured determine health and/or nutritional content based on a ratio between a reflected signal of a first frequency and a reflected signal of a second frequency.

In a still further aspect there is provided a system for managing plant growth over several zones comprising: storage configured to store quantitative data regarding plant matter according to location for each of the zones, a user input device configured to select a characteristic of the plant matter to display, and a controller or processor configured to analyse the data for displaying the selected characteristic over the locations for one or more of the zones.

BRIEF DESCRIPTION OF THE DRAWINGS

Embodiments will now be described by way of example only, with reference to the accompanying drawings, in which:

FIG. 2a is a front view of a plant matter sensor;

FIG. 2b is a front view of a cluster of the plant matter sensor of FIG. 2a;

FIG. 8A is a circuit diagram of a bandpass filter;

FIG. 8B is a bode plot of the frequency response of the bandpass filter of FIG. 8A;

DETAILED DESCRIPTION

In an example embodiment a plant matter sensor is configured to measure the quantity and quality of plant matter using reflected light in both visible and non-visible wavelengths. The plant matter sensor includes vertically spaced clusters of light sensors and measures the quantity and various qualities of the plant matter at distinct points along the height of the plant matter. Plant matter's reflectance at different wavelengths is indicative of the qualities of that plant matter, such as its metabolisable energy, protein content, pasture biomass, neutral detergent fibre, or moisture content. By traversing an area containing plant matter (such as a pasture or crop) the sensor collects data relating to the quality of that area, which can be visualised and interpreted to assist pasture management.

When used for pasture management, short term benefits include being able to more accurately place break fences and in the calculation of the amount of supplementary feed required, which would mean that animals are less likely to be underfed, which is detrimental to production, or overfed, which is wasteful of resources.

Longer term benefits centre around the ability to identify areas or zones within a paddock that are less productive than others, or have less palatable grass. This means that application of fertilisers, weed sprays, drainage, irrigation, over sowing of pasture, aeration of soil, pH levels, shelter belts of other weather related controls, pest or pathogen discouragement, removal of local physical or chemical impediments plant genetics management etc could be targeted at those particular zones.

Prior plant matter sensors have been suggested to measure the quantity of animal feed within grazing pastures. However, merely measuring the quantity of plant matter without reference to the quality of that plant matter may be inadequate for ensuring animals meet their nutritional requirements.

In particular, prior plant matter sensors have failed to measure and interpret important qualitative features of plant matter at an adequate scale and speed. Such qualitative features may include protein content, pasture biomass, Neutral Detergent Fibre and moisture content.

Figure 1:
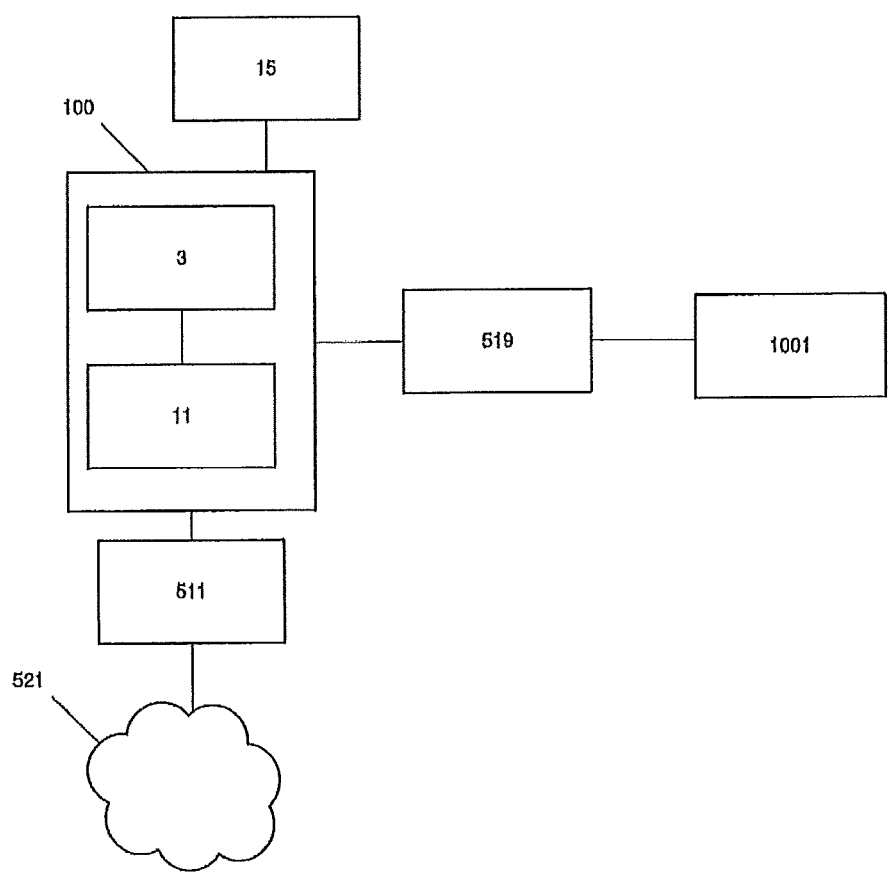
FIG. 1 is a schematic diagram of a pasture management system according to one embodiment.

FIG. 1 shows a schematic diagram of an example pasture management system. The pasture management system includes a plant matter sensor 100. The plant matter sensor includes a sensor board 3 and a main board 11. The sensor board includes emitters and transmitters for detecting plant matter. The main board communicates with the sensor board, a master controller 611 and optionally a restoring/actuating element 519. The plant matter sensor may further include an accelerometer 15.

The plant matter sensor is carried on one or more vehicle 1001, which traverses a field collecting plant matter data. Plant matter data collected by the plant matter sensor is stored, processed and/or displayed on the main board, master controller and/or the internet 521.

Plant Matter Sensor

FIG. 2a shows a front view of a plant matter sensor 100. The plant matter sensor includes a housing 1, which houses an elongate sensor board 3, and a main board 11. The sensor board 3 is substantially vertical in use. The main board 11 contains control and signal processing components.

Eight clusters 5 of emitters 7 and receivers 9 are vertically arranged along the sensor board. Each cluster 5 includes four emitters and four receivers. In use, the plant matter sensor is maintained with its lower end 13 at or slightly above ground level. Each emitter in a cluster provides illumination at one peak wavelength (Near Infrared-880 nm, Red Edge-740 nm, Red-680 nm, Green-527 nm). This specific combination of wavelengths is used to calculate important indices and ratios related to pasture quality.

The height of the sensor board may depend on the height of the plant matter being sensed. For rye grass, a plant matter sensor may include a sensor board up to 370 mm in height.

The number of clusters and the spacing between these may depend on the type of plant matter being analysed, or the resolution required. For rye grass, the sensor board may include between 4 and 8 sensor clusters, spaced between 10 mm to 30 mm from each other.

The clusters are aligned vertically; alternatively the sensor board may include clusters horizontally spaced from one another.

The emitters and receivers are arranged in the clusters so that the measurements taken from each receiver within the cluster can be used in combination to measure the characteristics of the plant matter in proximity to the particular cluster. The actual number of emitters and receivers in total and in each cluster may vary depending on the level of detail required from each reading pulse, and the nature of the plant matter.

The main board may be connected to further sensor boards (either vertically or horizontally), in order to measure plant matter of increased height and/or differing orientation.

Power is provided by either an on-board battery or via an automotive supply from the vehicle to which the plant matter sensor is physically attached.

FIG. 2b shows a front view of a cluster 5 of the plant matter sensor of FIG. 2a. The cluster includes four emitters 201, 203, 205 and 207, and four receivers 211, 213, 215 and 217. Each emitter emits a distinct wavelength (which may fall within both the visible and non-visible ranges) substantially perpendicularly from the sensor board. Each emitter is paired to a corresponding receiver configured to detect the corresponding wavelength.

Each emitter and receiver has an effective half angle optimised to maximise the reflected light from the transmitter and minimise exposure to ambient light and light from other transmitters. The proximity of transmitter and receiver pairs and the dimensions of the cavities in the housing in which they reside is also optimised to maximise the reflected light from the transmitter and minimise exposure to ambient light and light from other transmitters.

The emitters emit light within wavelengths which when reflected, and combined with other emitters, provide information about the quality of the plant matter being measured. Suitable emitters include LEDs and lasers. The emitters are matched to wavelengths which can be used to determine important plant quality characteristics. They must also be capable of being driven at sufficient intensity to provide a reflected signal that the receivers can detect.

The emitters are positioned on the sensor board at a distance between 6 mm and 10 mm from the paired receivers, so that the receivers are in the correct proximity for detecting reflected light from the emitters. The receivers may be between 44 mm and 55 mm from the target, for example approximately 50 mm from the target.

Any suitable number of emitters of any suitable wavelengths may be used at each cluster to measure and calculate parameters of interest from plant matter. Between 3 to 6 emitters emit both visible and non-visible radiation are suitable for obtaining relevant information about the plant-matter. Some wavelengths which may provide useful information about plant matter include: Near Infrared-880 nm, Red Edge-740 nm, Red-680 nm, Green-527 nm. Multiple emitters of the same wavelength may also be added to each cluster to increase the accuracy of the plant-matter sensor.

The receivers are sensitive to light within the wavelengths of their respective paired emitters. Suitable receivers include photodiodes and IR enhanced Charge-coupled Device (CCD) sensors.

Each receiver may be configured in photoconductive mode, for example with the photodiode reversed biased. This mode of operation is preferred as it produces a linear response to receiver illumination.

In other embodiments a single receiver may detect reflected light within a range of wavelengths. Emitters may emit non-synchronously, and many emitters may be paired to a single receiver.

Most emitters have a relative luminous intensity over a range of wavelengths and receivers have a relative spectral sensitivity over a range of wavelengths. The receiver/emitter pairing should be sensitive only to the wavelengths selected according to the application to provide indications of a specific quality of the plant matter.

If emitters which emit over a large range of wavelengths are employed, then any receivers that are receiving from the emitter should have sufficiently narrow sensitivity to ensure the measured signal consists largely of only the wavelength(s) to be measured.

Conversely, a receiver with a large spectral sensitivity range may be paired to an emitter which has a narrow relative luminous intensity range.

Optionally, a single emitter or receiver may be employed to scan different points on the plant stem. For example, the emitter may be physically rotated, an optical shutter may be translated or the device may be electronically steered.

Figure 3:
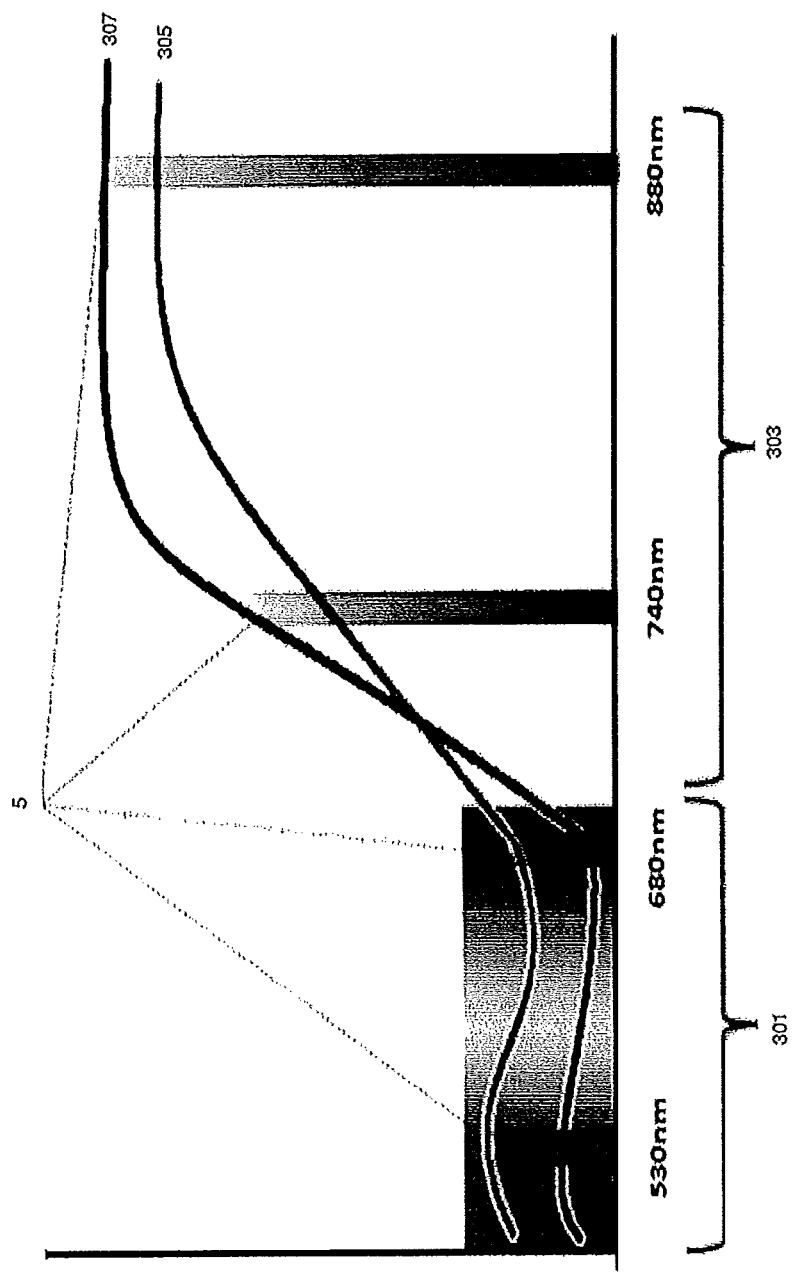
FIG. 3 is a graph of the relationship between emitter wavelengths and vegetation quality.

FIG. 3 is a graph of the relationship between emitter wavelengths and vegetation quality. The emitter 201 emits visible green light with a wavelength of around 530 nm, and is paired with receiver 211 which is configured to detect reflected light of that wavelength. Emitter 203 emits visible red light with a wavelength of around 680 nm, and is paired with receiver 213, which is configured to detect reflected light of that wavelength. Emitter 205 emits near infrared light with a wavelength of around 740 nm and is paired with receiver 215, configured to detect reflected near infrared light of that wavelength. Emitter 207 emits near infrared light with a wavelength of around 880 nm and is paired with receiver 217, configured to detect reflected near infrared light of that wavelength.

Plot-line 305 shows the amount of light reflected at each wavelength for a low-feed plant matter sample, and plot-line 307 shows the amount of light reflected at each wavelength for a high-feed plant matter sample. Compared to the low-feed sample, the high-feed sample reflects a relatively lower amount of visible light, as emitted by emitters 201 and 203 and detected by receivers 211 and 213 respectively. Compared to the low-feed sample, the high-feed sample reflects a relatively higher amount of near infrared radiation, as emitted by emitters 205 and 207 and detected by receivers 215 and 217 respectively. This demonstrates how feed-quality of plant matter can be determined by analysing the amount of radiation reflected by it at each wavelength.

Figure 4A:
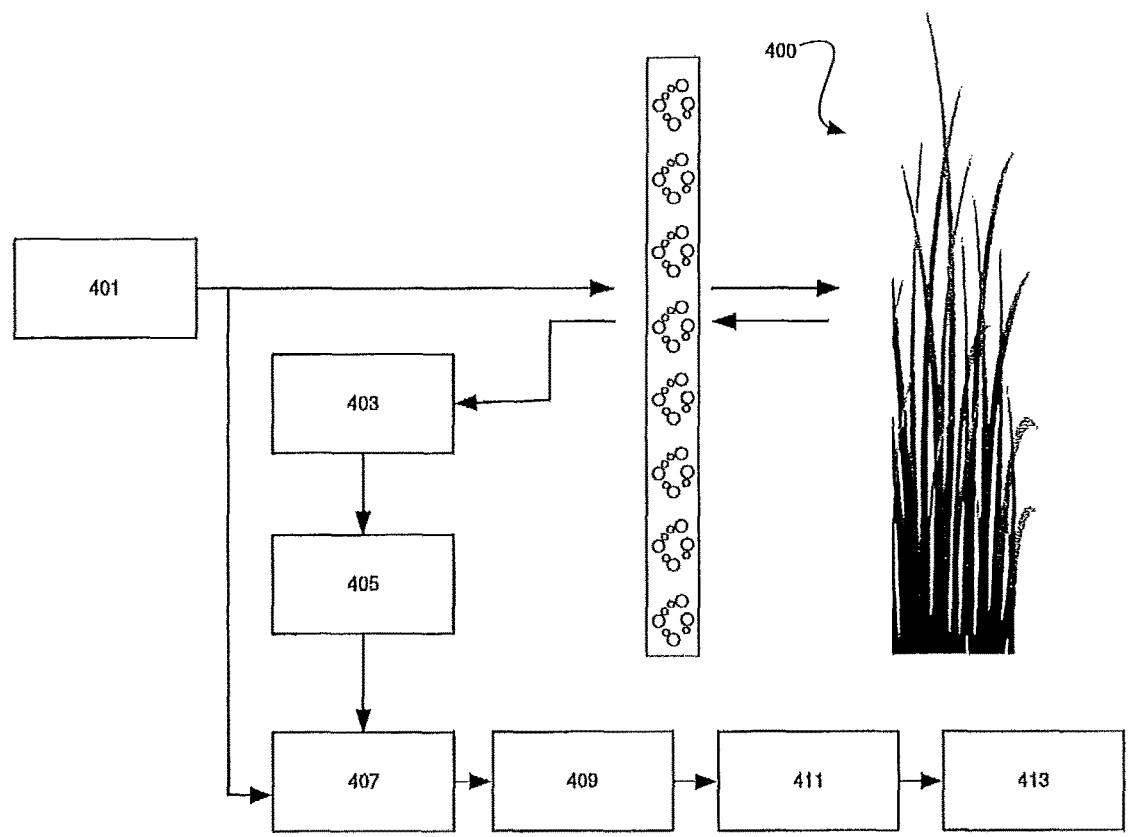
FIG. 4A is a process diagram of measuring the quality of plant matter using a plant matter sensor.

FIG. 4A shows a process diagram of measuring the quality of plant matter 400 using a plant matter sensor. A microcontroller 401 triggers the emitters to emit a waveform of known (reference) frequency, which is reflected back from the plant matter and detected by a paired receiver. By modulating the emitter signal at the reference frequency, this allows the effect of noise and ambient light to be eliminated from the reflected signal. A synchronous detector demodulates the reflected signal.

Emitters which are not in close proximity are driven in combination with no adverse effects on the measurements being taken. The emitters are connected to 8 drive signals from the main board. The physical groupings are such that emitters which are driven by a single drive signal will not interact with one another. Individual emitters may be further isolated by increasing the number of drive signals and switching them more independently. The multiplexer operates on the receivers and connects each receiver sequentially to the signal processing/data acquisition circuitry.

The signals from the receivers are then switched through a high speed analogue multiplexer 403 which allows all the signals to be passed through the same signal processing pathway in order to take a final digital measurement. An alternative arrangement may use multiple signal processing pathways, for example, one per wavelength being tested. This arrangement would allow for differing signal gains to be implemented on different wavelengths being measured. The use of an SPI bus multiplexer allows the plant matter sensor to include multiple sensor boards. The SRI bus allows multiple elements sensor boards to be individually selected using one signal (CHIP SELECT PIN) per board. The output signal from each board being connected to a common SPI data bus. The multiplexer reduces the number of signals which must be transmitted between individual sensor boards and the main board from thirty-two down to eight: the SRI bus requirement (DATA, CHIP SELECT, CLOCK), the power supply lines (+12v, −12v, +5v, GND), and the output line from the multiplexor which carries the pre-amplified signal receiver element. In the absence of the multiplexor one line would be required for each of the receivers.

The signal from the multiplexer 403 then passes through a pre-amplifier 405. The location of the pre-amplifier on the sensor board provides the shortest possible trace path for the unamplified signal.

The preamplified signal enters the synchronous detector 407, (an AD630 balanced modulator/demodulator), as does the reference signal. The amplifier demodulates the reflected signal, by multiplying it with the reference signal. The amplitude of the demodulated signal provides a direct indication of the reflectance at the frequency of the emitted radiation.

The demodulated signal is passed through a bandpass filter 409, followed by a low pass filter 411. The final voltage is then converted to digital by an analogue-to-digital converter 413. The measurement can then be used to calculate meaningful data relating to the quality and/or quantity of the plant matter being sampled. In an alternative design, more advanced devices may be used, for example, a demodulator featuring built in signal conditioning and/or programmable filters (e.g. Analog Devices ADA2200).

Figure 4B:
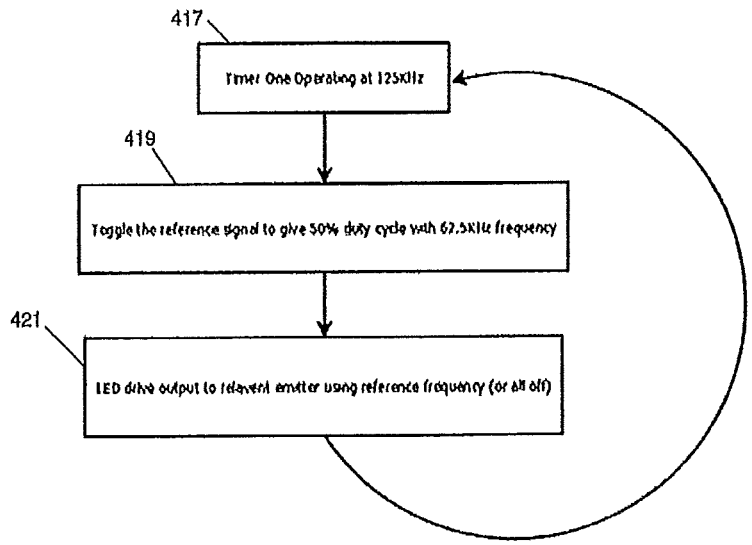
FIG. 4B is a flow diagram of a method of driving an emitter.

FIG. 4B shows how the emitter is driven. At 417, timer one operates at 125 KHz. At 419, this timer generates a reference signal of 62.5 KHz frequency and 50% duty cycle. Timer one is also responsible for directing the reference signal to the currently selected emitter at 421. In FIG. 4C a second timer (timer zero running at 125 Hz), which is running independently of timer one, is responsible for cycling through the emitters and receivers in sequence. Timer zero selects a transmitter, allows some settling time, then selects the paired receiver and takes an ADC reading of the signal. For each iteration of timer zero, readings are taken for every receiver on the sensor. Emitter and/or receiver timing may also be achieved in software using an additional microcontroller, or in hardware by using a crystal oscillator or a more advanced demodulator IC with an inbuilt clock generator and/or divider.

The combination of the two timers means that individual emitters are pulsed with the reference frequency (62.5 kHz) for a duration of 168 μs every 8 ms as shown in FIG. 4C. The entire sensor (all individual emitter/receiver pairs) can therefore be read at 125 Hz (1/0.008 s=125 Hz). In an alternative timing arrangement, different wavelength emitters may be pulsed with differing modulation frequencies. In such an arrangement the demodulation and signal processing pathway for each wavelength would be matched to the relevant emitter modulation frequency. The modulation signal may also be connected/disconnected from individual or groups of emitters through means of hardware switching such as a multiplexor or other digital switching device.

Figure 4D:
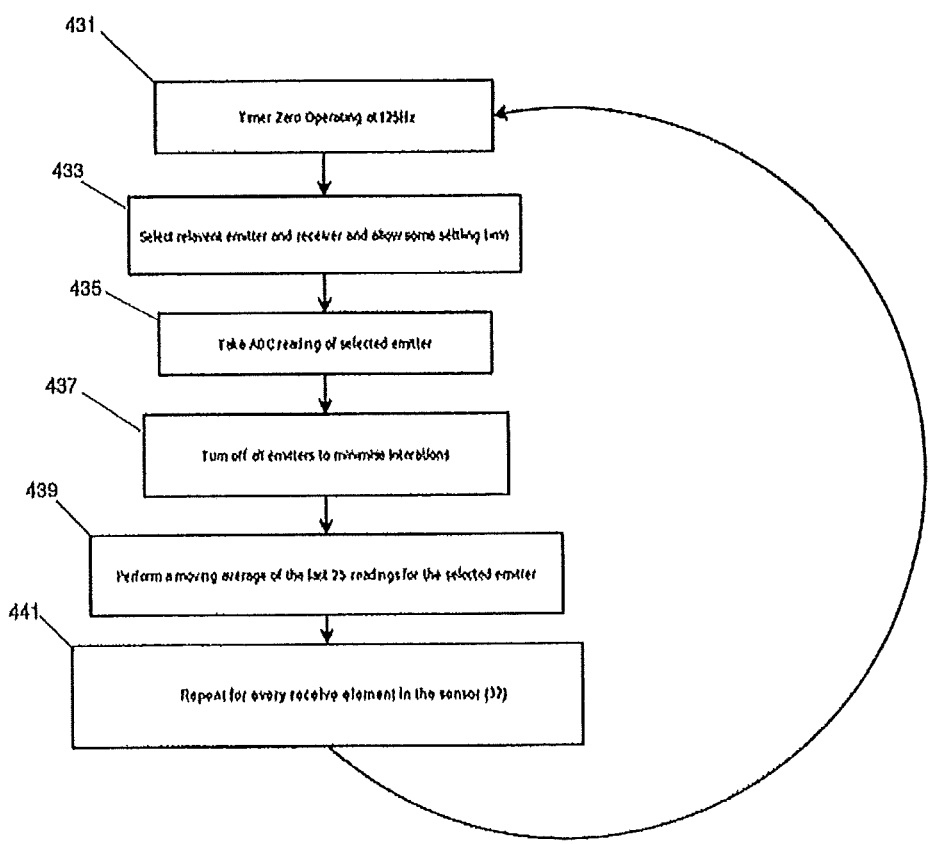
FIG. 4D is a flow diagram of a method of collecting data from the receiver.
Figure 4C:
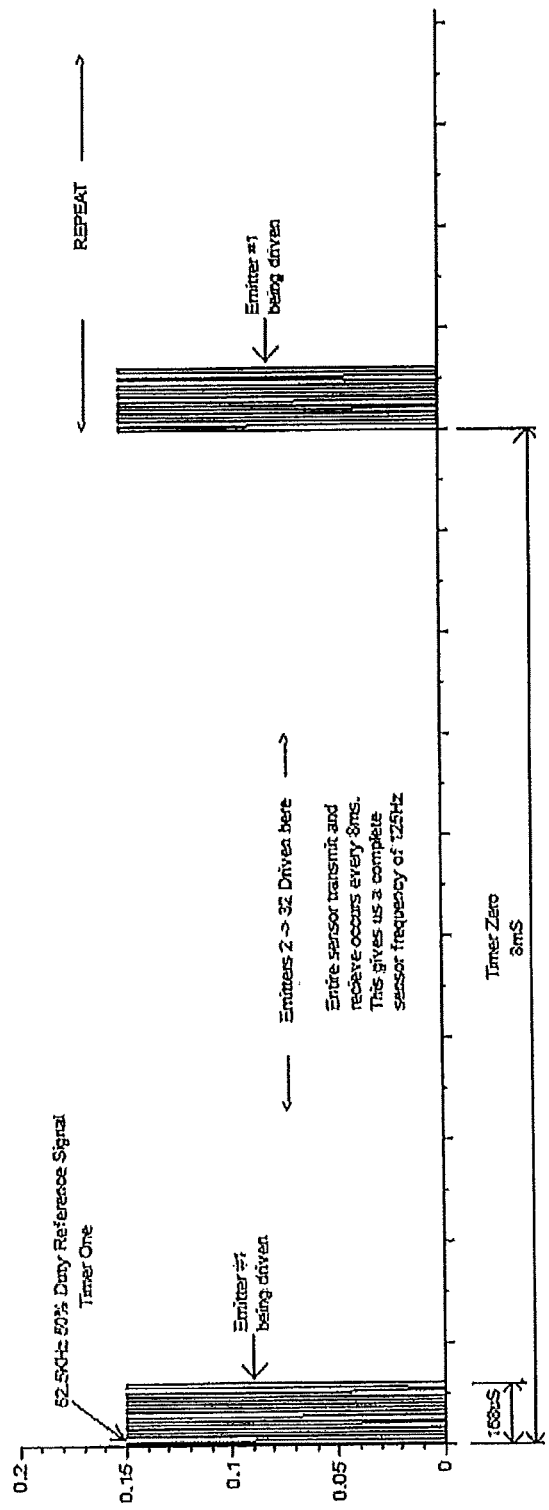
FIG. 4C is a graph of the signal from each emitter.
Figure 5:
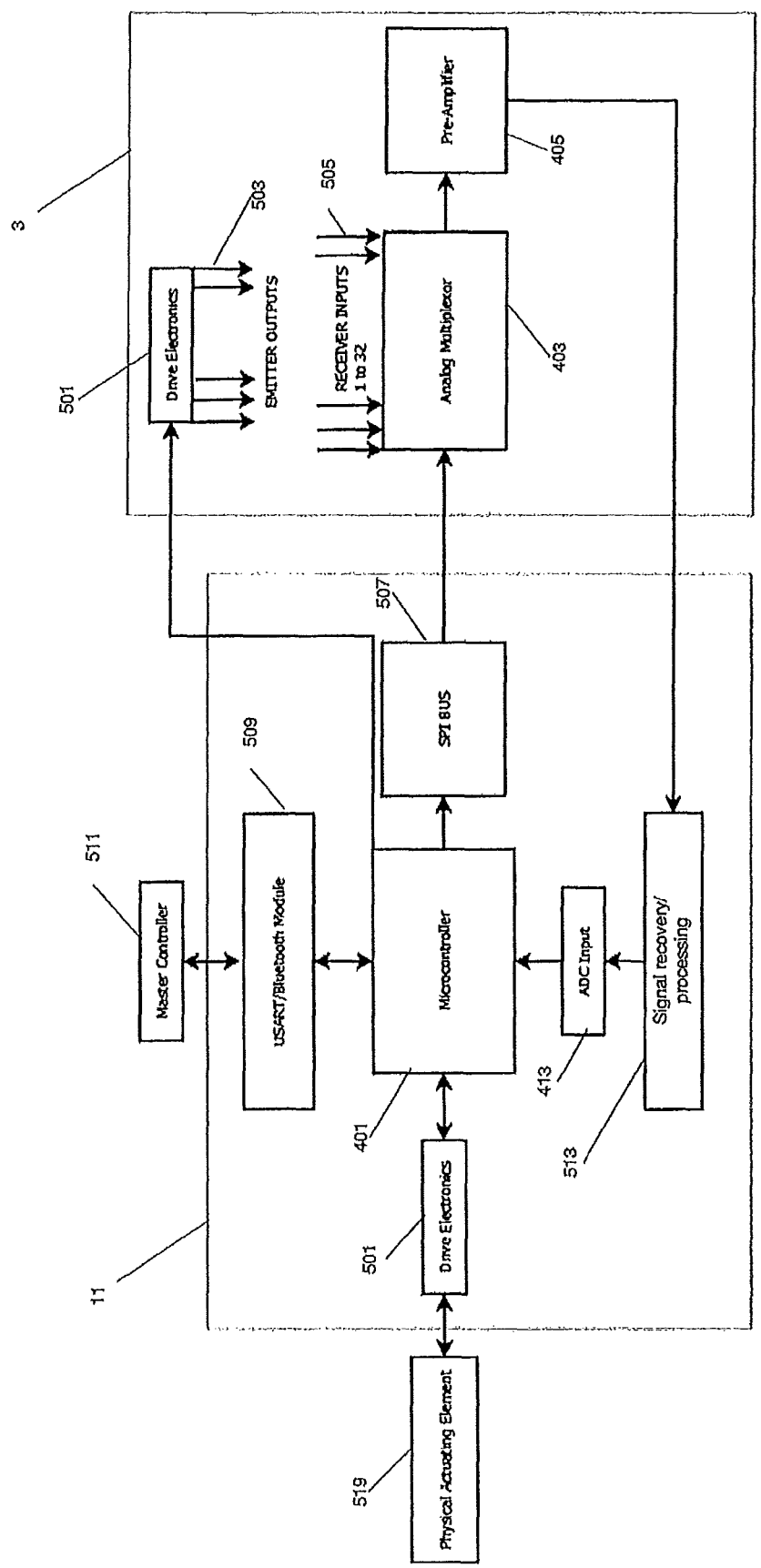
FIG. 5 is a schematic diagram of a plant matter sensor.

FIG. 4D shows how the data is collected by the receiver. Timer zero operates at 125 Hz (431). The relevant emitter and receiver pair is selected and allowed some settling time (433). An ADC reading is made of the selected emitter (435), after which all emitters are turned off to minimise interactions (437). A moving average of the last 25 readings for the selected emitter is made (439). A moving average of 25 readings minimises low frequency flicker noise from the signal receiver/signal processing pathway. The process is repeated for the remaining receivers in the sensor (441). The speeds are based on an assumed forward speed of 18 kph (5 ms$^{-1}$) and a nominal sward width of 40 mm (5 m/125 Hz=40 mm). FIG. 5 shows a schematic diagram of the plant matter sensor. The main board 11 communicates with the sensor board 3, physical actuating element 519. The actuating element 519 is an electric linear actuator combined with a damper and/or spring arrangement and a master controller 511 (described in more detail below). In particular, the main board performs the signal processing to recover the signal from the controlled light source.

The sensor board includes drive electronics 501, the analogue multiplexor 403 and the pre-amplifier 405. The signal is transmitted from the preamplifier to the mainboard's signal recovery/processing unit 513 and then to the analogue digital converter 403.

The main board includes the microcontroller 401, an SPI Bus 507 transferring data to the analogue multiplexor, drive electronics 501, for driving the physical actuating element 519, and a USART/Bluetooth module 509 (wireless link) for communicating with a master controller 511.

The emitters are driven in eight clusters, each cluster switched using a power MOSFET and a series resistor in order to limit the current. The emitters within one drive bank may be either in series or parallel depending on their required forward voltage. The supply voltage to the emitters is regulated in order to ensure a consistent output level.

The transmission of the signal through the high speed multiplexer 403, preamplifier 405, synchronous detector, bandpass filter and low pass filter will now be described in detail.

Figure 6A:
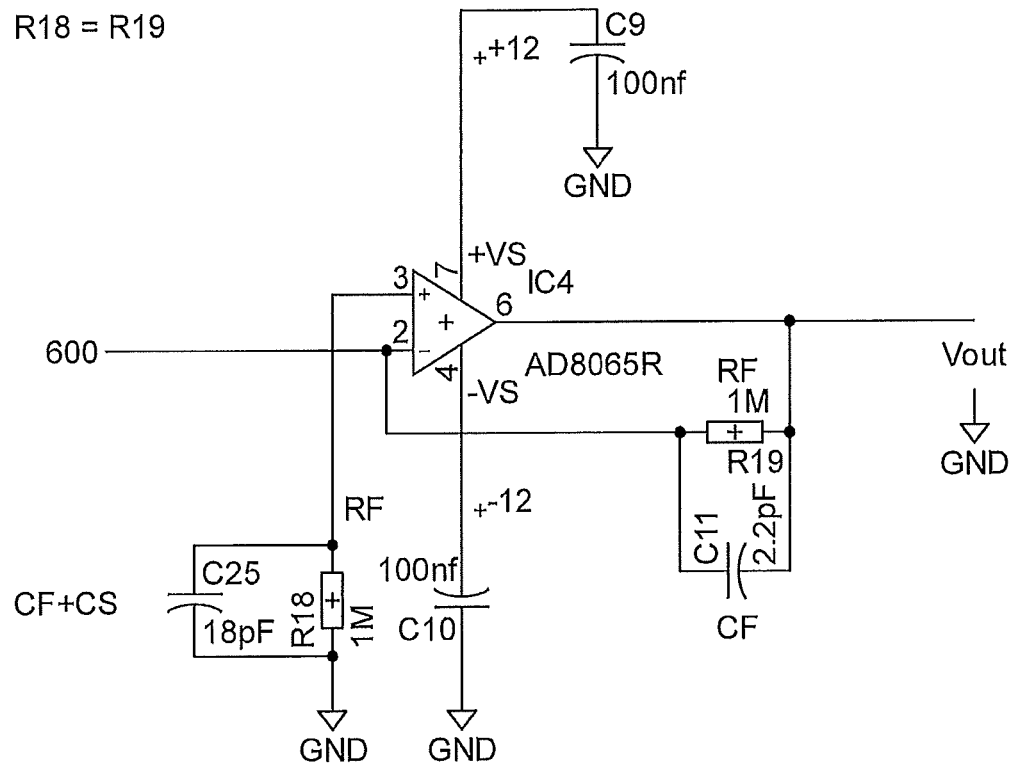
FIG. 6A is a circuit diagram of a wideband photodiode preamplifier.

The preamplifier 405 consists of a high speed operational amplifier configured as an inverting amplifier. FIG. 6A shows a circuit diagram of a wideband photodiode preamplifier, receiving a signal 600 from the multiplexor 403.

The basic transfer function is given by equation 1:

$$V_{OUT} = \frac{I_{PHOTO} \times R_F}{1 + sC_F R_F} \quad (1)$$

| | | |
|---|---|---|
| CF | 2.2E−12 F | |
| RF | 1000000 Ohms | |
| CS | 1.1E−11 F | From Datasheet |

Calculating the resulting transfer function in equation 2:

$$V_{OUT} = \frac{50}{1 + 0.0000022S} \quad (2)$$

Figure 6B:
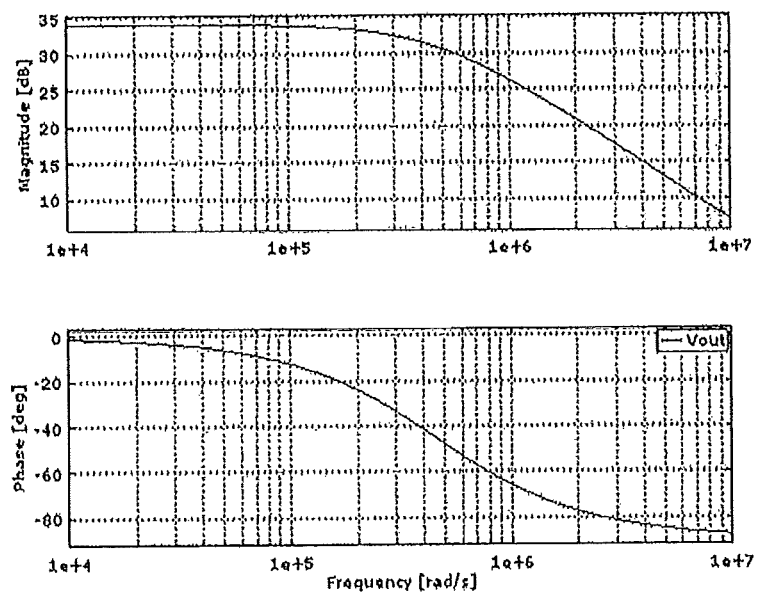
FIG. 6B is a bode plot of the frequency response of a preamplified signal.

FIG. 6B shows a bode plot of the frequency response of the preamplifier of FIG. 6A.

Figure 7:
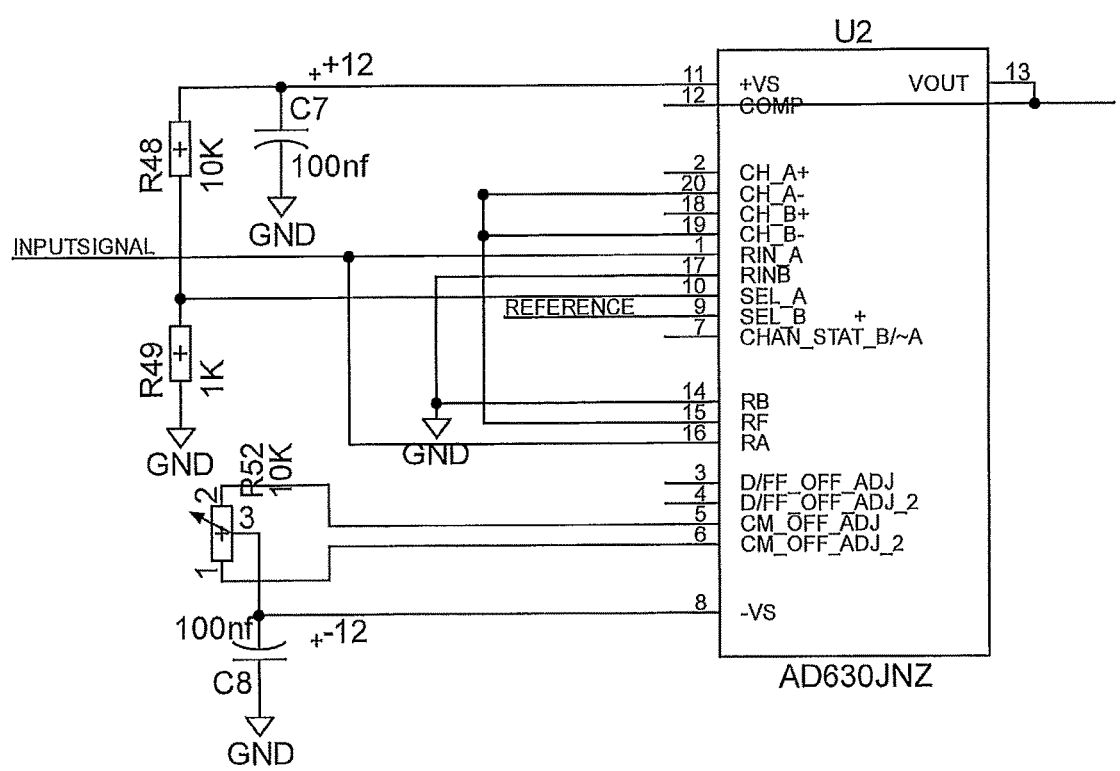
FIG. 7 is a circuit diagram of a synchronous detector.

The pre-amplified signal is then transferred to the synchronous detector 407. The synchronous detector may include an AD630 o ADA2200 balanced modulator/demodulator integrated circuit, as shown in FIG. 7. The synchronous detector takes two signals. The first is the reference signal of known frequency, which is also used to pulse the emitters on the sensor. The second is the signal from the receiver (photodiode) which has been passed through a preamplifier.

The synchronous detector outputs a multiplication of the input signal with the reference signal.

Then, to recover the reflected light signal into a measurable voltage it is passed through several filters. The filters smooth out the rapidly varying waveform so measurements can be taken by the analogue to digital converter on the microcontroller, a process which takes 13 uS.

The first filter is a Sallen-Key bandpass filter. FIG. 8A shows a circuit diagram of a bandpass filter according to one embodiment.

| | Calculated Value | Available Value |
|---|---|---|
| $F_0$ | 2500 | 2.5K |
| C1 | 0.000000022 | 22 nf |
| R4 | 100000 | 100K |
| Q | 1 | |
| K | 0.000345575 | |
| R5 | 120000 | 120K |
| C2 | 0.00000001 | 10 nf |
| R1 | 5600 | 5.6K |
| R2 | 2000 | 2K |
| R3 | 12000 | 120K |
| H | 1.833333333 | |

Calculated transfer function in equation 3:

$$\frac{V_O}{V_{IN}} = \frac{32738.095 S}{S^2 + 15367.97 S + 5.655^{-08}} \quad (3)$$

FIG. 8B shows a bode plot of the frequency response of the bandpass filter of FIG. 8A.

After the signal has been passed through the band-pass filter and the negative portion of the signal has been removed using a diode, the signal is then passed through a final low pass filter with corner frequency given by equation 4:

$$f_c = \frac{1}{2\pi RC} = \frac{1}{2\pi \times 1000000 \times 47 \times 10^{-12}} = 3386 \text{ Hz} = 21274 \text{ rad/s} \quad (4)$$

And transfer function in equation 5

$$H(s) = -\left(\frac{R_f}{R_i}\right)\left(\frac{1}{1+RCs}\right) = \frac{-1.779}{1+0.000047S} \quad (5)$$

Figure 9A:
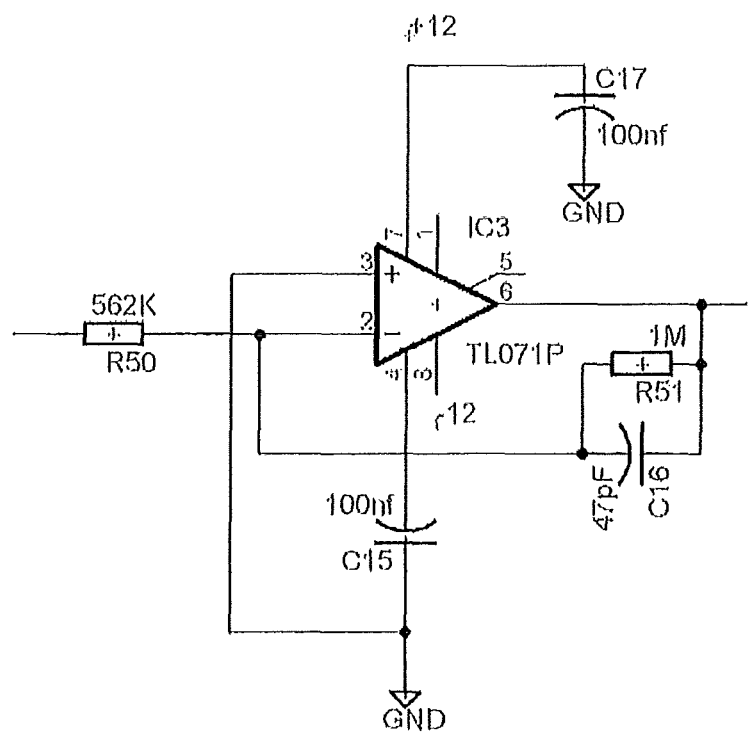
FIG. 9A is a circuit diagram of a low pass filter.
Figure 9B:
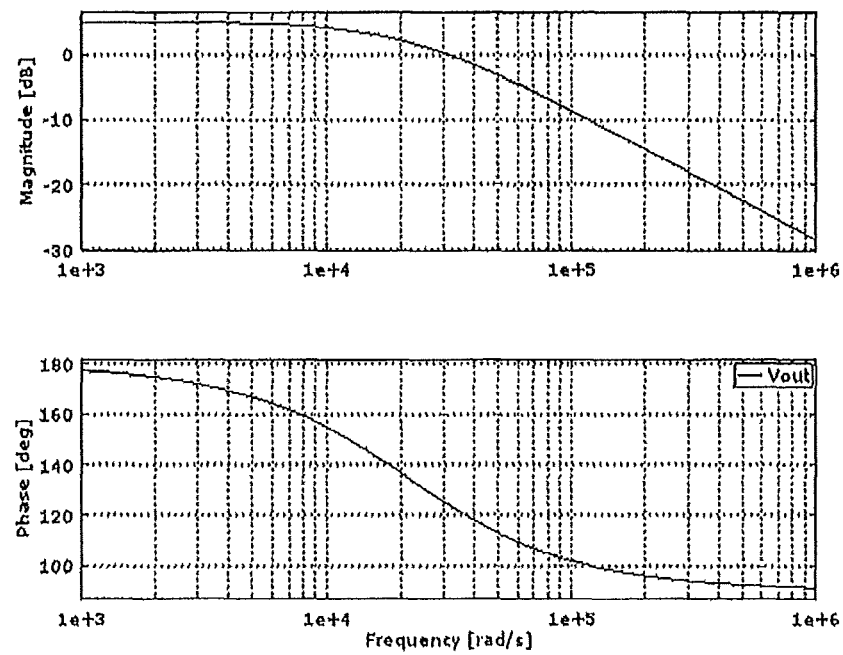
FIG. 9B is a bode plot of the frequency response of low pass filter of FIG. 9A.

FIG. 9A shows a circuit diagram of a low pass filter according to another embodiment. FIG. 9B shows a bode plot of the frequency response of the low pass filter of FIG. 9A.

Finally, the measurements are taken by the analogue to digital converter on the microcontroller. The measurements are then interpreted by a processor and associated software algorithms and/or firmware. The microcontroller measures the amplitude of each reflected signal as an integer (0-1023) and transmits this to the master controller. The accuracy of the signal measurement may be further improved by employing an external analogue to digital converter with a higher resolution and/or conversion speed. Statistical methods may be used to further reduce noise in the measurements, for example a moving average or oversampling.

The housing of the plant matter sensor may be CNC machined or injection moulded plastic. The housing maintains the sensor and main boards in a waterproof environment, and minimises fouling of the sensor board from dirt or other material.

The main body of the plant matter sensor may comprise Acrylonitrile butadiene styrene (ABS) thermoplastic polymer. The emitting beams radiate through a lens or material which is resistant to UV and abrasion. An example is a machined Lexan MR10 cover. The surface may be made hydrophobic to minimise moisture on the sensor.

Figure 10A:
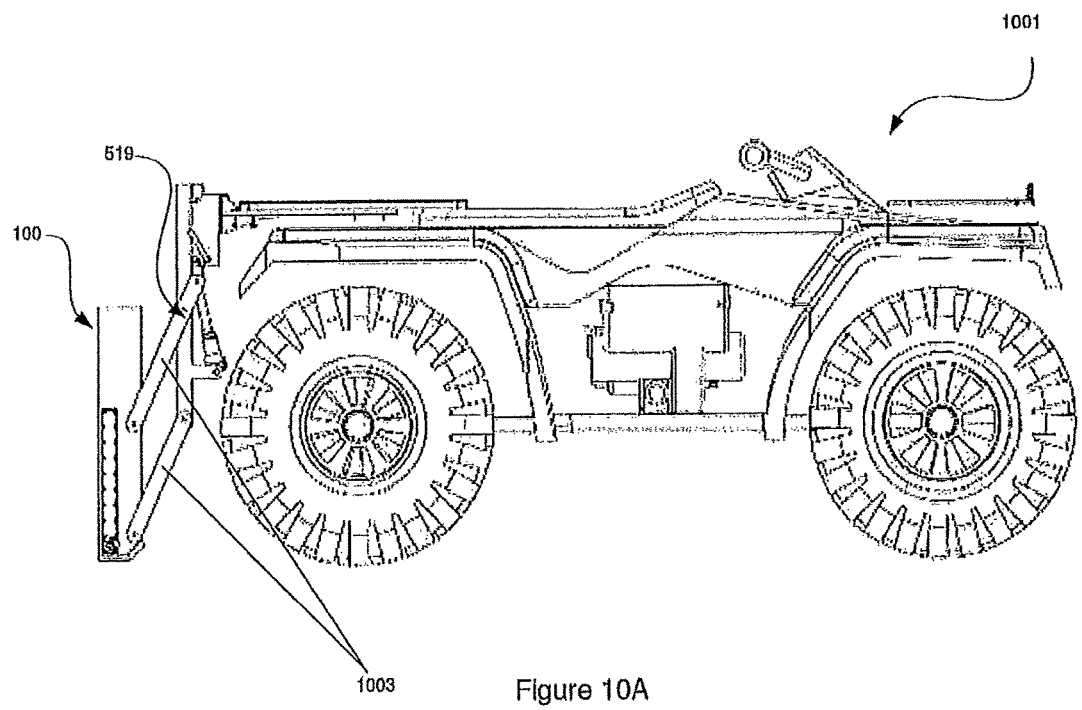
FIG. 10A is a perspective view of a vehicle carrying a plant matter sensor.

The housing of the plant matter sensor may be configured to minimise ambient light reaching the receivers. For example, the receivers may be partly shrouded inside the housing ambient light from the sensors, as shown in FIG. 10A.

The frame and/or plant matter sensor may further include deflector guards (not shown) to keep the wet grass and other contaminants from the emitters and receivers. Air pressure may also be used to clear the lenses and holes through which the emitters and receivers send and receive.

Sensors may be kept clean by a knife edge arrangement running vertically along the edge of the beam, or mechanical and/or spray arrangement to wipe and clean the sensors. When the sensor is in the raised position, checks may be made to ensure no beams are reading material in this raised position.

Vehicle Attachment

Figure 10B:
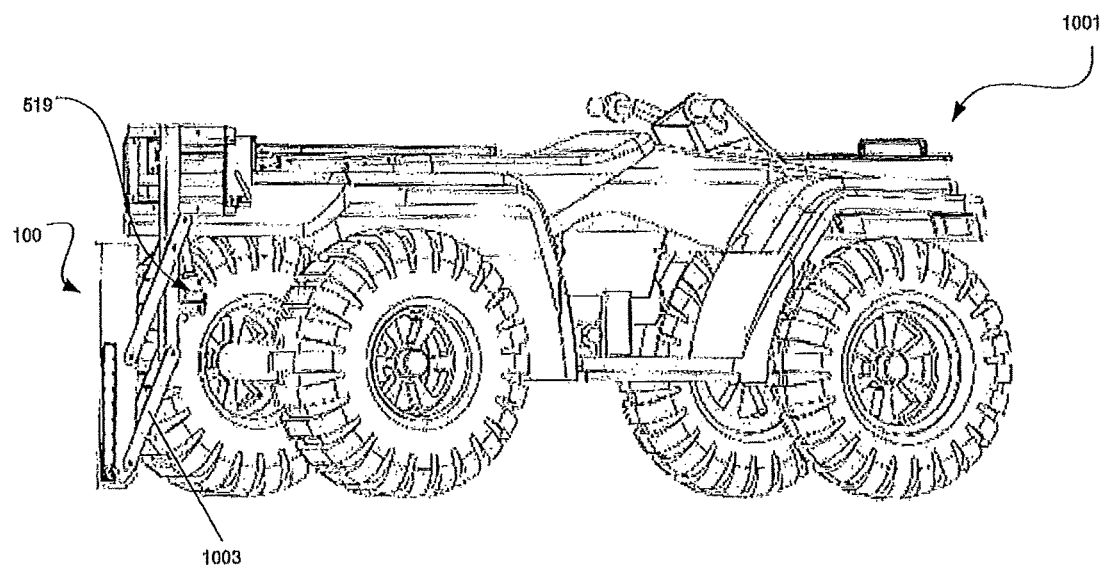
FIG. 10B is a side view of the vehicle of FIG. 10A.

In order to rapidly measure entire pastures, the plant matter sensor is attached to or towed by a vehicle which traverses a pasture, crop or other land-area to be measured. Suitable vehicles include ATVs, tractors, and mowers. An example of a plant matter sensor attached to a vehicle is shown in FIGS. 10A and 10B. The plant matter sensor is attached to the back of a vehicle 1001 by a mounting frame 1003, which maintains the sensor board at or just above ground level. Optionally, the plant matter sensor includes a less-rigid frame, combined with wheels to follow the contours of the paddock being traversed.

The plant matter sensor may be positioned away from the grass for high speed transport when not in use. This may also be automated by employing some positional awareness. For example, inside a paddock the actuating element lowers the sensor to the measuring position and in a raceway the actuating element raises the sensor to a transport position.

In other embodiments, the plant matter sensor may be on a vehicle which is remotely controlled. Alternatively, the sensor may be on an autonomous vehicle which automatically traverses a pasture. It may follow a preprogramed set of waypoints or use logic or AI to cover designated areas. Such an autonomous vehicle may be configured to be able to detect and avoid unpassable terrain and obstacles (such as fences and livestock).

As the plant matter sensor scans grass or other plant matter on a vehicle which may be moving at considerable speeds, preferably, the emitters and receivers operate at a sufficient speed that the individual measurements relate to plant matter from the same plant. The emitter/receiver pairs make between 125 to 200 readings per second.

The quality and/or quantity of the pasture may be measured every 7-10 days, however the frequency of this depends on the type of plant matter, level of management desired and/or the season.

The plant matter sensor includes or communicates with a GPS receiver so that each set of data collected by the plant matter sensor is geo-referenced as to its collection position. One data point is stored at a minimum interval of one second together with a Latitude and Longitude. The non-differentially corrected GPS has an accuracy of less than five metres ninety five percent of the time. A higher accuracy can be achieved using differentially corrected GPS.

Plant matter sensor measurements taken in between GPS measurements are associated with interpolated GPS latitude and longitude coordinates.

The display of accurately rendered pasture cover data onto a GPS farm map gives the ability to identify variations in productivity within areas of paddocks, and thereby plan livestock rotation, fertiliser application, irrigation and drainage requirements to maximise overall paddock productivity while at the same time avoid wastage of resources through application to areas not requiring those resources.

Pasture management software may take the latitude and long coordinates from the GPS point and couple that with the date to automatically reference the correct formula for that time and region.

GPS readings may be used to suggest to the operator of the vehicle where to drive in order to capture sufficient plant matter sensor data points of the field.

Physical/actuating Element

It is important that the sensor board is maintained at a uniform distance to the ground in order to properly distinguish which parts of the plant are being measured. An arrangement which applies a constant downward force may be used to hold the sensor housing in contact with the ground. For example, this may be a spring and/or dampening arrangement.

A ground-contact sensor may be included to determine when the plant matter sensor is contact with the ground.

The three-axis accelerometer may also monitor ground impacts, and at ground impacts above a certain threshold (indicating that the sensor will lose contact with the ground), may suspend readings and/or inform the user to reduce the speed of the vehicle to prevent further high impacts which may cause the sensor to lose contact with the ground.

Accelerometer

The plant matter sensor may incorporate a 3 axis accelerometer 15 which is regularly sampled to check for any physical impacts which exceed safe operating limits. The use of an accelerometer allows the operator to be notified of the excessive forces and modify their operation accordingly. The operator may be notified via messages displayed or audible tones on or from the master controller.

A more automated system could be realised by using the accelerometer data in conjunction with the actuating element 519 in order to raise the plant matter sensor out of harm's way.

This system could be further expanded to incorporate a "memory" of ground that is rough or contains obstacles. Where readings exceed safe levels, the GPS coordinates would be saved and on future rides the user could be prompted with a warning when re-entering these areas. A ride trail may be provided with prompts about which path to follow in each paddock to ensure adequate coverage. The ride trail may be displayed as a layer which is overlaid onto the map on the controller screen. This could also show places not to go i.e. avoidance zones

Master Controller

The master controller may be a computer, a laptop, a tablet or other computing device capable of running applications which capture, process, display and distribute the measured/calculated metrics.

Data points may be stored on the plant matter device itself, a database on the master controller, and/or the cloud. Data sent from the main board to the master controller may include a moving average of each emitter i.e. 32 individual readings per time period 8× Near Infrared-880 nm, 8× Red Edge-740 nm, 8× Red-680 nm, 8× Green-527 nm.

Data point may include:
- Raw wavelength values at each receiver and/or cluster and an identification means to link data back to its respective signal source
- Latitude and longitude
- Date and time
- Indices
- Qualitative metrics (e.g. metabolisable energy, and crude protein content)
- Ground temperature The indices could be calculated on either the plant matter sensor itself or the master controller. For easier updating of metrics, preferably the indices are calculated on a master controller with remote (WIFI) updating abilities.

The master controller may also have a GNSS receiver to geotag indices and qualitative metrics as well as displaying metrics and position in real-time. It may also illustrate or describe the vertical profile or composition of the current sample (or average of many samples). The master controller will upload data directly to the cloud based decision support as well as storing the information in case it is needed at a later date or corruption occurs.

Desirably the main board and/or master controller monitors the emitters and/or receivers for fault conditions. For example, a receiver that consistently shows no received signal, when adjacent receivers are receiving signals as the plant matter sensor passes through the pasture, is interpreted as a fault. In such circumstances a display and control console can alert the operator to check the emitters and receivers.

Calibration of the plant matter sensor can be undertaken manually to enable seasonal factors to be taken into account. However, automatic calibration is contemplated by detecting grass quality.

The plant matter sensor preferably has a number of user-selectable measuring modes, interpreting the output from the clusters in slightly different ways. For example, a uniformly dense dairy pasture may require a different approach from a dry sparse pasture with seed heads. The measuring mode may be auto selected so as to suit the pasture condition.

The main board drives actuating elements 519 to ensure the sensor boards are located in the desired position and/or orientation to take measurements. The reaction time of the actuator does not need to be fast as the sensor is held against the ground using a spring/damper arrangement. The actuator raises or lowers the sensor into or out of the measuring position.

Spectral vegetation indices may be used to optically measure plant matter "greenness". These are mathematical combinations/ratios of different spectral bands.

The normalized difference vegetation index (NDVI) may be used to assess the amount of live green vegetation in plant matter using the plant matter sensor. NDVI is calculated from the visible and near-infrared light reflected by vegetation. Healthy vegetation absorbs most of the visible light that hits it, and reflects a large portion of the near-infrared light. Unhealthy or sparse vegetation reflects more visible light and less near-infrared light.

The NDVI is calculated using the equation 6:

$$NDVI = \frac{NIR - VIS \text{ (Red)}}{NIR + VIS \text{ (Red)}} \quad (6)$$

where VIS stand for the spectral reflectance measurements acquired in the visible (red) region and NIR stand for the spectral reflectance measurements acquired in the near-infrared regions.

Another index which may be used is the generalised difference vegetation index (GDVI), with equation 7:

$$GDVI = \frac{NIR - VIS \text{ (Green)}}{NIR + VIS \text{ (Green)}} \quad (7)$$

The simple ratio index is the ratio of light that is scattered in the NIR range to that which is absorbed in the red range in equation 8:

$$SR = \frac{NIR}{RED} \quad (8)$$

The range of values is generally between 0 to 30+. Healthy vegetation generally falls between values of 2 to 8.

The specific frequencies used to calculate the indices are: Near Infrared-880 nm, Red Edge-740 nm, Red-680 nm, Green-527 nm. However other frequencies may be used depending on the plant matter or sensing application. Each modulated emitter/receiver combination measures from its respective wavelength. Raw signals may be averaged such that indices are calculated once per second.

Other various formulas and equations for determining the above and additional plant qualities from reflectance data will depend on the application.

The appropriate indices to be used with the plant matter sensor are those that best explain the relationship between the reflected radiation from the emitter/receiver combination and the metrics of interest. The indices used may be adjusted based on season, time of day, physical location (region) or even cluster, as each of these parameters may influence how qualitative information is represented.

As clusters of emitters and sensors are arranged vertically, the sensor is capable of measuring plant matter height. Plant matter height may be measured using a threshold on the amount of reflected light measured. A reading above the threshold indicates the presence of material at a certain height, and conversely a reading below the threshold indicates the absence of material at that height. Thus, the height of any particular plant matter sample can be deduced by establishing the upper-most cluster proximate to plant material and using the height of that cluster as the approximate plant matter height.

Optionally the plant matter sensor can do post-processing of the recorded data to convert a series of height readings into pasture density calibrated as kilograms of dry matter per hectare (kg/DM/Ha). These algorithms are relatively sophisticated, and take into account seasonal variations, long stalky grass where not all sensors are eclipsed contiguously, rough grass where there is a great variation in the height readings, pre and post-grazing situations, pasture species, and disregard occasional interference by contaminants on one or more of the emitters or photo transistor.

Alternatively, or in addition to height information, a number of qualities of interest may be calculated, including (but not limited to) metabolisable energy (MJME), protein content, pasture biomass, neutral detergent fibre (digestibility), senescence and decay (dead matter). Each cluster of four sensors is able to derive such qualities from the ground level to the upper extent of the plant material. As previously discussed, the sensor employs emitters at different wavelengths matching parts of the visible and non-visible spectrum whose levels, when reflected off plant matter, provide the relevant qualitative information. Other features or qualities could be measured such as insects or other pests present, physical damage to the plant matter (caused by pests or physical damage from animals over grazing or simply trampling due to crowding in a particular area due to meteorological conditions and animal comfort) bacterially or fungal growth or other pathogens. Depending on the application other qualities may be important and other relevant ratios may apply. The measurements could determine the types of plant matter present and distinguish the species (eg: whether there are too many weeds in a given location) or varieties (eg: different grass species/cultivars) in each location.

Figure 11:
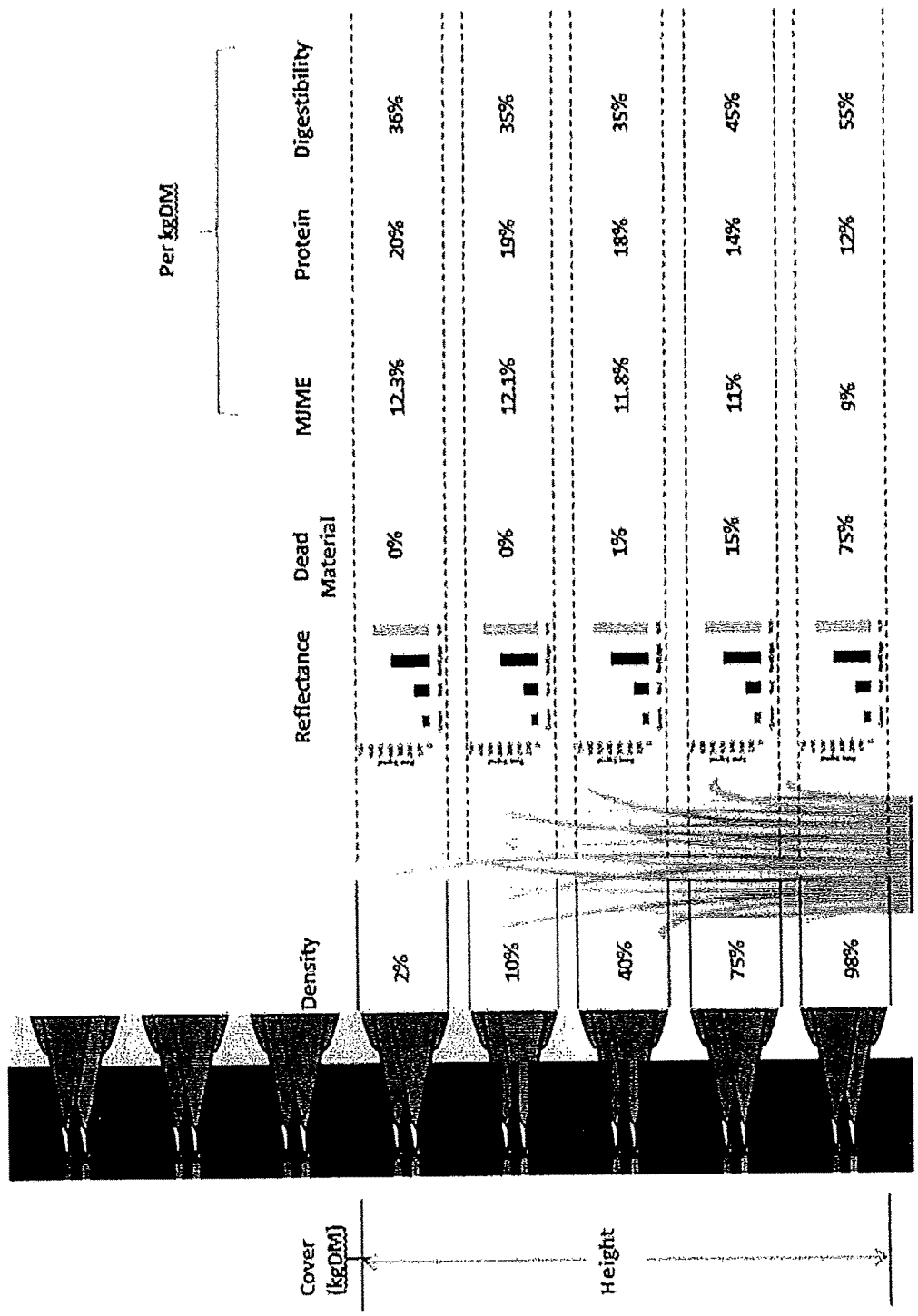
FIG. 11 is a visual representation of sensor measurements and information output.

FIG. 11 is a visual representation of sensor measurements and information output according to another embodiment. Relevant information is displayed for each cluster level, which matches a distinct area of the plant matter 400. As only the first four out of eight clusters detect any significant amount of plant material, the height of the plant can be approximated as the height of the fourth cluster. The density at each cluster is calculated as a proportion of the number of reported signals received over a given time period for each cluster. In the infographic of FIG. 11, the lowermost part of the plant has a density of 98%, and the uppermost a density of 2%. The amount of dead material, metabolisable energy, protein and digestibility at each cluster are also shown.

Figure 12:
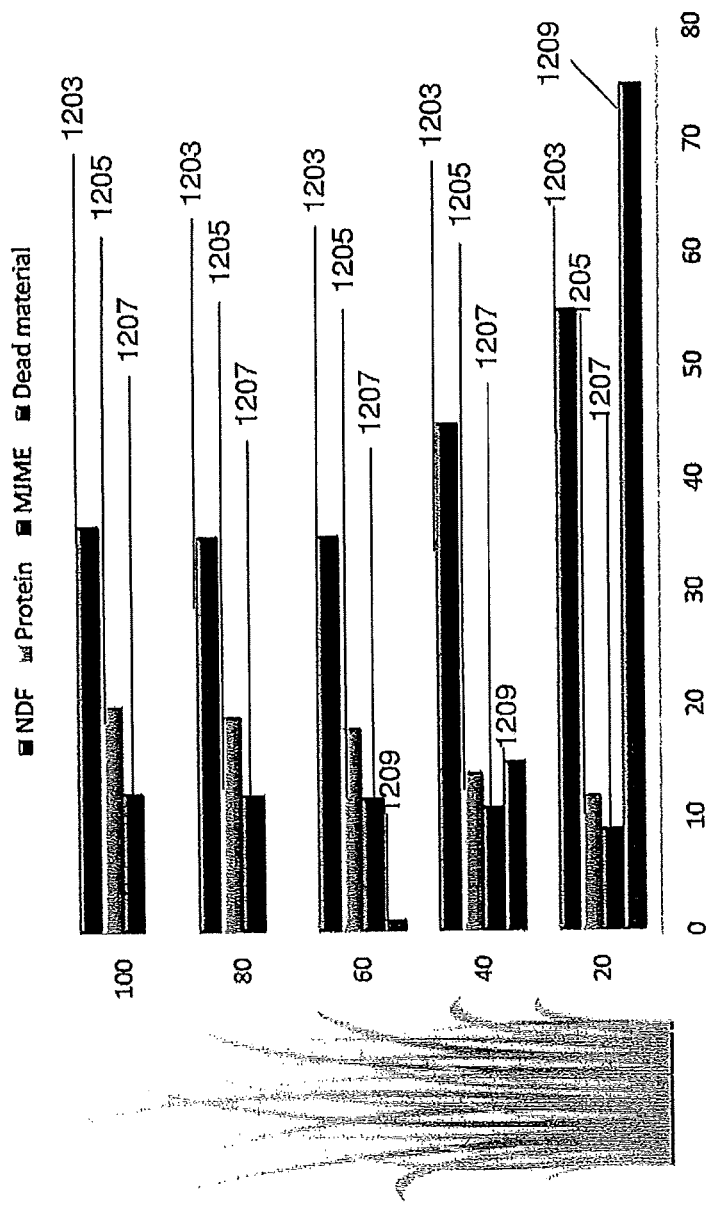
FIG. 12 is a bar graph showing an example of the information contained in a single data point.

FIG. 12 shows a bar graph providing an example of the level of information that every data point (average of 125 hz) contains. In this example, a data point including information from five clusters. The Y axis represents the height of the plant, in mm, and the X axis represents the relative quantities of neutral detergent fibre 1203, protein 1205, metabolisable energy 1207 and dead material 1209. One data point is stored a minimum of every second together with a Latitude and Longitude along with other information, such as speed information. The information may be stored on the physical plant matter sensor or on a separate computer device.

The information may be displayed by a suitable application or tool, for example "SmartMaps". A user may be able to narrow in on single point data if site specific information is needed.

Figure 13:
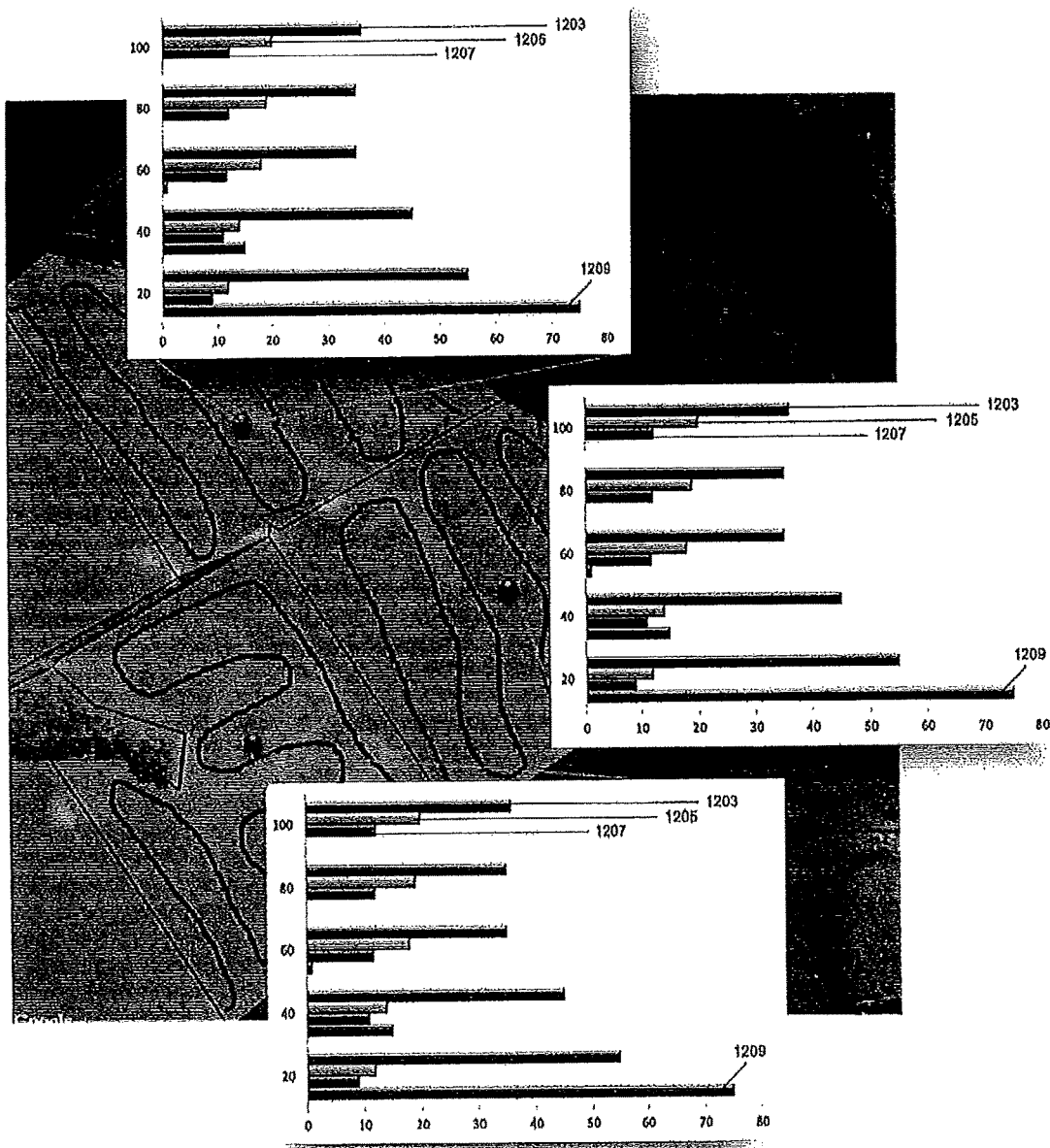
FIG. 13 is a paddock scale visualisation.

Information may also be viewed in the form of paddock scale visualisations, as shown in FIG. 13. In this view data is averaged for a paddock or spatial region and allows for rapid comparison of performance or matching animal (or herd) nutritional demand to paddock nutritional supply.

Figure 14:
FIG. 14 is a spatially interpolated paddock scale visualisation.

Key qualitative metrics may be spatially interpolated. This interpolation is performed on single point information so it presents a novel method for creating and viewing many layers of stratified data from the same metric. FIG. 14 shows an example of information displayed in this way. In this view, spatial trends can be observed and actions taken to maximise nutrient or energy harvest or to perform remedial action in the case of a large contiguous block of high percentage dead plant matter. Remedial action may include cultivating and replanting if the dead matter is over a threshold.

Figure 15:
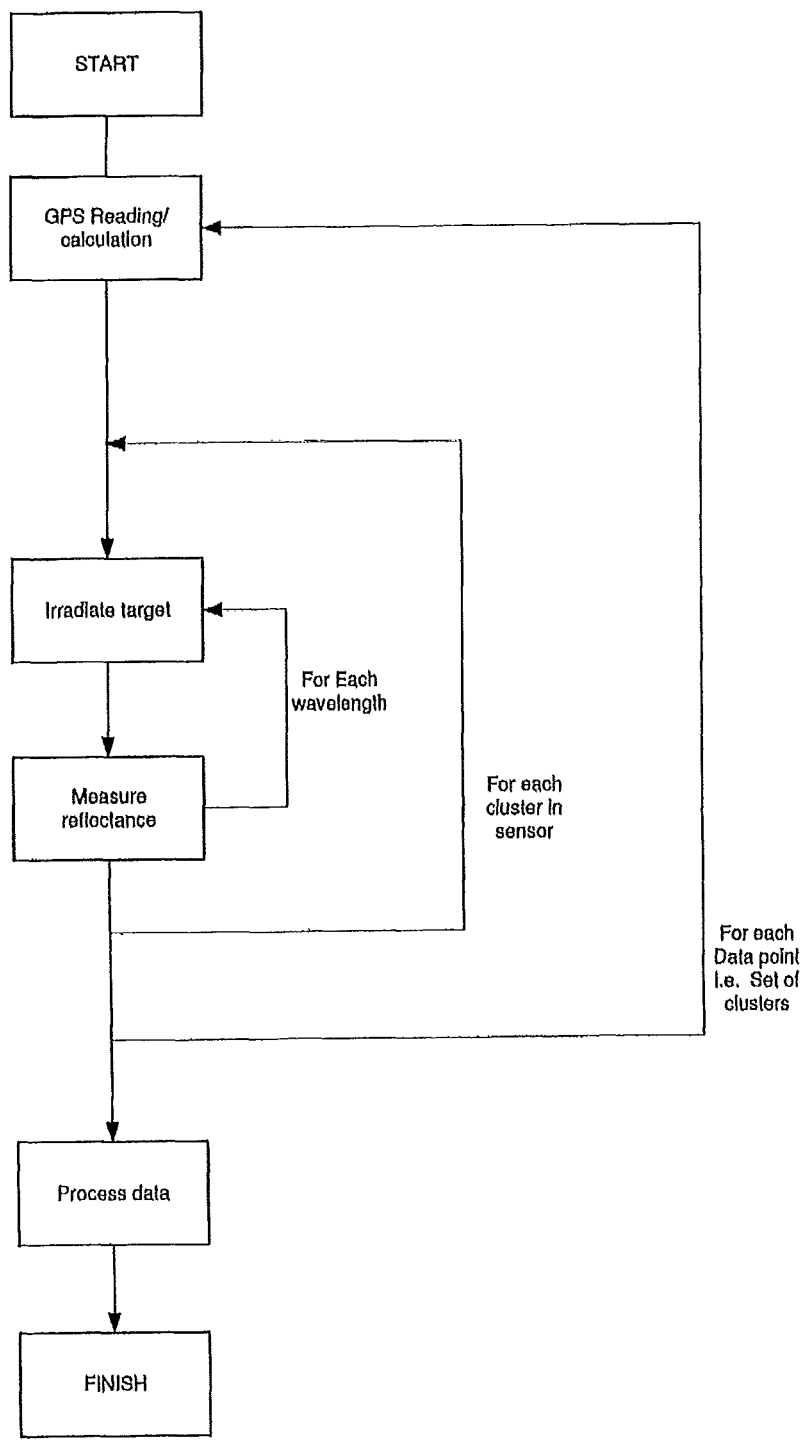
FIG. 15 is a process diagram of a system of determining the quality of plant matter.

FIG. 15 is a process diagram of a system of determining the quality of plant matter.

For each data point (representing a set of clusters) a GPS reading is made and included in the data point.

Ambient light may be measured to minimise its effect on readings. This may or may not be necessary depending on receiver sensitivity, physical placement of the sensors (e.g. shrouding by a housing/cavity) and the modulation of the emitter/receiver.

For each cluster in a sensor, the wavelengths of interest are measured. For each emitter/receiver pair within a cluster, the target plant matter is irradiated and the reflectance of the plant matter is measured.

The data point may then be sent to a master controller for storage and/or processing.

The plant matter sensor measures both the quality and quantity of plant matter in a pasture, at a fast speed and a large scale. Protein content, pasture biomass, neutral detergent fibre and moisture content may be measured and used to improve pasture management through grazing, soil nutrition or irrigation for example.

By measuring qualitative data along the length of the plant, the plant matter sensor is capable of distinguishing the quality of the plant material along different parts of the plant (e.g. stem, or tips).

The information obtained can be used at all levels of farm management, including at the operational (day to day grazing), tactical (feed budgeting), and strategic (Zone management, yield mapping, VRT) levels.

This could be implemented in real time by a vehicle and applying an automated dynamic remedial action. For example if the soil in that location was determined deficient in a particular mineral the vehicle could apply the deficient mineral. Further management software could track the effect of previous applications of corrections eg: fertiliser or insecticide/herbicide, it could calculate a more accurate corrective action for each location. The modified correction could be based on artificial intelligence or empirical data.

The remedial action could be forwarded in near real time (to sensing) to a following vehicle such as fertiliser spreader, or after analysis and management consideration and decision making.

Automated remedial action will depend on the application. For example in pasture for animals, a low protein measurement may be automatically correlated to the application of more nitrogen. Other examples include selective over-sowing where particular pasture cultivars are sown into the soil depending on one or several sensed parameters combined with the terrains slope and aspect and season. More complicated remedial actions may be determined when the user uploads their data to a cloud based processing and analytics system. Once processed the decision could be sent to the land manager to accept/reject or sent directly to the specific machine that it needed to perform the action. The cloud based processing may be setup to learn from pervious corrective suggestions and follow-up measurements either on the particular farm or across many farms or regions.

While embodiments have been illustrated by the description, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept. For example while embodiments have been described in relation to a plant matter sensor the invention may find application for sensing level of nutrients, pollutants, or other particular or matter in bodies of liquid (eg: aquaculture or hydroculture) or gaseous mediums.

The invention claimed is:

1. A plant matter sensor comprising:
   one or more emitters configured to emit two or more light signals toward a plant matter; and
   one or more receivers configured to receive two or more reflected light signals from the plant matter;
   wherein emitters and receivers are arranged together in clusters on an elongate sensor board;
   wherein the plant matter sensor includes a housing configured to minimise ambient light reaching the receivers; and
   a processor configured determine health and/or nutritional content based on a ratio between a reflected signal of a first frequency and a reflected signal of a second frequency determined at vertically displaced points on the plant matter.

2. The plant matter sensor of claim 1 wherein the one or more emitters emit at a plurality of visible and invisible light frequencies.

3. The plant matter sensor of claim 1 configured to output data to a user interface for displaying plant matter health and/or nutritional content.

4. The plant matter sensor of claim 1 further comprising a positioning system configured to georeference the reflected signals.

5. The plant matter sensor of claim 1 wherein the one or more emitters emit visible and near-infrared radiation.

6. The plant matter sensor of claim 1 wherein the emitted signals are emitted sequentially.

7. The plant matter sensor of claim 1 wherein the receivers are read sequentially.

8. The plant matter sensor of claim 1 configured to measure at least one of: metabolisable energy, protein content, pasture biomass, neutral detergent fibre or moisture content.

9. The plant matter sensor of claim 1 wherein the emitted signals are encoded to minimise noise.

10. The plant matter sensor of claim 1 including a synchronous detector to demodulate the reflected signals.

11. The plant matter sensor of claim 1 wherein the plant matter sensor is configured to attach to a vehicle.

12. The plant matter sensor of claim 11 further comprising an actuator configured to substantially maintain the plant matter sensor in ground contact relative to the vehicle.

13. The plant matter sensor of claim 12 further comprising an accelerometer configured to detect physical impacts on the plant matter sensor with the ground.

14. The plant matter sensor claim 1 wherein the plant matter sensor is configured to determine the quantity of plant matter.

15. The plant matter sensor of claim 1 wherein the emitters are configured to be substantially vertically spaced in use.

16. The plant matter sensor of claim 1 wherein the plant matter sensor transmits at least 125 signals per second.

17. A system for managing plant growth over several zones comprising:
   a plant matter sensor of claim 1;
   storage configured to store measured qualitative and quantitative data regarding plant matter measured by the plant matter sensor according to location for each of the zones,
   a user input device configured to select a characteristic of the plant matter to display, and
   a controller or processor configured to analyse the data for displaying the selected characteristic over the locations for one or more of the zones.

* * * * *